US006237589B1

(12) United States Patent
Denyer et al.

(10) Patent No.: US 6,237,589 B1
(45) Date of Patent: May 29, 2001

(54) DISPENSING SYSTEM

(75) Inventors: Jonathan Stanley Harold Denyer, Pagham; Anthony Dyche, Hayling Island; Jacek Lech Basista, Tunbridge Wells, all of (GB)

(73) Assignee: Medic-Aid Limited, West Sussex (GB)

( * ) Notice: Subject to any disclaimer, the term of this patent is extended or adjusted under 35 U.S.C. 154(b) by 0 days.

(21) Appl. No.: 09/202,748

(22) PCT Filed: Jun. 20, 1997

(86) PCT No.: PCT/GB97/01682

§ 371 Date: Mar. 22, 1999

§ 102(e) Date: Mar. 22, 1999

(87) PCT Pub. No.: WO97/48431

PCT Pub. Date: Dec. 24, 1997

(30) Foreign Application Priority Data

Jun. 20, 1996 (GB) .................................................. 9612968

(51) Int. Cl.$^7$ .................................................. A61M 11/00

(52) U.S. Cl. ............................... 128/200.21; 128/200.14; 128/230.17; 128/204.23

(58) Field of Search ......................... 128/200.21, 200.18, 128/200.22, 200.14, 200.16, 203.23, 203.24, 204.26, 204.23

(56) References Cited

U.S. PATENT DOCUMENTS 6,000,394 * 12/1999 Blaha-Schnabel et al. .... 128/200.19

* cited by examiner

*Primary Examiner*—Aaron J. Lewis
*Assistant Examiner*—V. Srivastava
(74) *Attorney, Agent, or Firm*—Wiggin & Dana; William A. Simons

(57) ABSTRACT

A product dispensing system comprises a calibrated nebulizer having a nebulizer jet, mouthpiece, means for sourcing compressed air, a manifold for distributing the source of compressed air in at least one direction, a nebulizer accommodation means which is accessed by port, and a valve means for controlling the manifold and thereby the flow of compressed air to the port. The manifold and the port are linked by a length of tube, wherein the internal volume of the tube from the manifold outlet to the nebulizer jet is less than 0.7 ml.

24 Claims, 10 Drawing Sheets

TO LOAD

NEBULIZER CLEAN & EMPTY

CHARGE THROUGH FUNNEL

PUSH SPOUT ON AND SLAM SHUT.
NEBULIZER READY TO DELIVER

TO CLEAN

CLEAN AND DRY
ALL PARTS
THEN EITHER ...

REASSEMBLE BY STEPS
SHOWN IN FIGURES 8c,
8b, 8a IN REVERSE ORDER

B. SNAP COLLAR,
FUNNEL & SPOUT
TOGETHER AS A
UNIT THEN SNAP
UNIT ONTO BODY

DISPENSING SYSTEM

BACKGROUND OF THE INVENTION

1. Field of the Invention

This invention relates to a dispensing system, in particular one which may be of use for example in the dispensing of small quantities of medicament, where the medicament is required to be dispensed in aerosol from.

2. Brief Description of Art

It is known for dosing systems which supply a nebulized substance to containing a metering system. For example, in GB 1,568,808 (Rosenthal) there is described a metering system for supplying a nebulized substance for patient inhalation comprising a nebulizing means, a detecting means for detecting the initiation of the patient's inhalation, an adjustable timing means for adjusting a timed operation, and a valve means which is controlled by the timing means, in order to provide a controlled dosage of nebulized substance.

However, for this system to work and provide a precise dose of medicament, it is necessary that the system utilises a calibrated nebulizer which has a precise rate of output against time. Commercially available nebulizers have a wide range of outputs against time. In addition, the calibration must remain constant over the use of the nebulizer, and the nebulizer must be connected to the dosing device in such a way that the calibration of the nebulizer is valid and recognised when operated with the dispensing device. This is particularly important in relation to the length of tube between the value and the nebulizer.

Also, it is noted that this application describes no teaching of a device which is in any way calibrated for use with nominated drugs. This may have been due to the fact that the apparatus embodied in this application is designed for provocation testing, which is generally carried out in a laboratory, and is used to deliver pulses of aerosol into a patient's airway in order to determine their reactivity to allergens. The apparatus is not designed as one for a patient to take home, and to deliver precise does of medicament on a day to day basis.

In addition to the above application, GB 2,164,569 (Etela-Hameen Kauhkovammayhdiatys RY (Finland)) describes a similar system to that described above, which is also designed for provocation testing, except that it has an additional atomizing starting time control, which is used for selecting the atomizing starting moment to coincide with the beginning of the inspiration phase, which is found by examination to be favourable for a particular patient.

EP 519,742 (DeVilbiss Healthcare Inc.) describes a medical nebulizer control system which has three way valve. In the embodiment, one part of the valve is connected to a pressure sensor, and another is connected to a compressed air supply. The control system within this apparatus uses the supply tube to the nebulizer to detect the patient's breathing pattern. When it detects inhalation, it switches the valve over to the compressed air supply, which them drives the nebulizer for a predetermined period of time irrespective of whether the patient has continued to inhale or not. This device also suffers from the problems of other nebulizers in that there is a long length of tube between the control box and the nebulizer. In addition the nebulizer can be supplied from any manufacturer, and hence its calibration is not tied into the device, thereby causing variable amounts of medicament to be dispensed.

BRIEF SUMMARY OF THE INVENTION

According to the present invention, there is provided a product dispensing system comprising a calibrated nebulizer having a nebulizer jet, a mouthpiece, means for sourcing compressed air, a manifold for distributing the source of compressed air in at least one direction, a nebulizer accommodation means which is accessed by a port, and a valve means for controlling the manifold and thereby the flow of compressed air to the port, the manifold and the port being linked by a length of tube, wherein the internal volume of the tube from the manifold outlet to the nebulizer jet is less than 0.7 ml.

Preferably, the internal volume of the tube from the manifold outlet to the nebulizer jet is less than 0.5 ml.

Conveniently, the dispensing system according to the invention is utilized in conjunction with a small air compressor as the source of compressed air, which has a flow rate in the region of 1–2 litres per minute.

By "calibrated" in this instance is meant that the dosage rate for the nebulizer has already been established, and the dosimeter programmed accordingly, so as to provide a known dosage rate for a given medicament. It is envisaged that a given dosimeter will have one or more dedicated nebulizers.

In preferred embodiments of the invention, the dispensing system additionally comprises a switch means, which is responsive as to whether compressed air is flowing in the system.

It is another preferred aspect of the invention that it may comprise a dispensing system comprising a dosimeter which has been pre-programmed to dose one or more medicaments according to predetermined dosage profiles.

The dispensing system according to the invention is conveniently one which is capable of being pre-programmed to dose one or more different types of drugs, which may need to be dosed according to different profiles. Methods of pre-programming the dispensing system in such a fashion will be familiar to those skilled in the art. In addition, the nebulizer and dosimeter according to the invention are calibrated to determine the dosage of drug as described in EP 587,380 (Medic-Aid Limited), the contents of which are incorporated herein by reference.

The dispensing system according to the invention incorporates a nebulizer and a mouthpiece, by which nebulized medicament can actually be delivered to the patient. The dispensing system can also additionally preferably comprise a pressure sensor, which is capable in use of detecting a pressure drop in the apparatus in response to the patient's breathing, and then delivering a pulse of nebulized medicament into the mouthpiece. In such instances, the dose of medicament can be calculated by the known rate of output against time for the drug selected, and the sum of all nebulizer pulses which the system has delivered, in ways known to those skilled in the art, as referred to above. Such ways may typically include performing clinical trials on the drug to determine appropriate dosages, and programming these electronically into the dispensing system.

It is to be understood that the manifold in a dispensing apparatus according to the invention can, in fact, be an integral part of the valve means, and need not be a separately discreet entity. In certain embodiments, the manifold is a shaped block with internal galleys, for example, made of plastics materials, and its presence allows the tubes to be connected to the ports on the valve. The ports on the valve may be too close together to accommodate the connection of tubes directly, and a manifold increases the space between them in other embodiments it may be necessary for the manifold to distribute compressed air in at least two different directions.

The dispensing system according to the invention can operate from a variety of different compressed air sources, such as a continuous air supply at a rate of around 6 litres per minute. This can typically be provided either from a pressurized cylinder such as those used in hospitals, or can be generated from a conventional air compressor.

In an alternative and preferred configuration, the dispensing system can be operated with a lightweight compressor system, which typically generates a low flow rate (in the order of 1–2 litres per minute, preferably 1.5 litres per minute), in conjunction with an accumulator. Such a combination of low flow rate compressor and accumulator allows the dispensing system to produce pulses of compressed air to a nebulizer in dispensing system with the flow around 6 litres per minute, where the flow from the compressor is matched to the mean flow through the nebulizer (1.5 litres per minute). In addition, such a combination of low flow rate compressor with accumulator, in conjunction with the dispensing system according to the invention, provides a dosing apparatus which is more lightweight, compact and readily portable than known dosing apparatuses.

With regard to the manifold, if the dispensing device according to the invention is used in conjunction with a low flow rate compressor, it is only necessary for the valve to switch the compressed air on and off to the nebulizer, in which case the manifold may only need to direct the compressed air in one direction only. However, if the dispensing system is used in conjunction with a conventional air supply such as a six litre per minute compressor or gas bottle supply, the manifold in conjunction with the valve directs the flow to either the nebulizer or the outlet orifice. In such circumstances, the valve in conjunction with the manifold has either one port or two outlet ports, depending on the application.

An important feature of the dispensing systems according to the invention lies in the volume of the tube linking the manifold and the port being less than 0.7 ml, preferably less than 0.5 ml. It has been found that by using lengths of tube which have a relatively small volume, the nebulizer starts to work as quickly as possible once the patient's inhalation has been detected. Typically, it is possible that the nebulizer can work within 50 milliseconds of detecting the patient's inhalation. To facilitate both the rapid response time and the low volume of the tube linking the manifold and the port, it is preferred that the valve is physically close to the nebulizer.

If a relatively long tube, or one with a large internal volume is used between the manifold and the nebulizer, this tube has to be pressurized before the nebulizer starts to operate. This can have significant effects on the performance of the system with regard to the controlling the rate of output of the nebulizer, since the nebulizer should preferably be provided with an essentially constant rate ("square wave") of pressure over time, so that its output is constant over time. The nebulizer used in the dispensing system is preferably one which delivers inspiratory patterns between 0.1 and 1.5 seconds duration.

BRIEF DESCRIPTION OF THE DRAWINGS

The invention will now be described further by way of example only with reference to the accompanying drawings, in which.

DETAILED DESCRIPTION OF THE PREFERRED EMBODIMENTS

Figure 1:
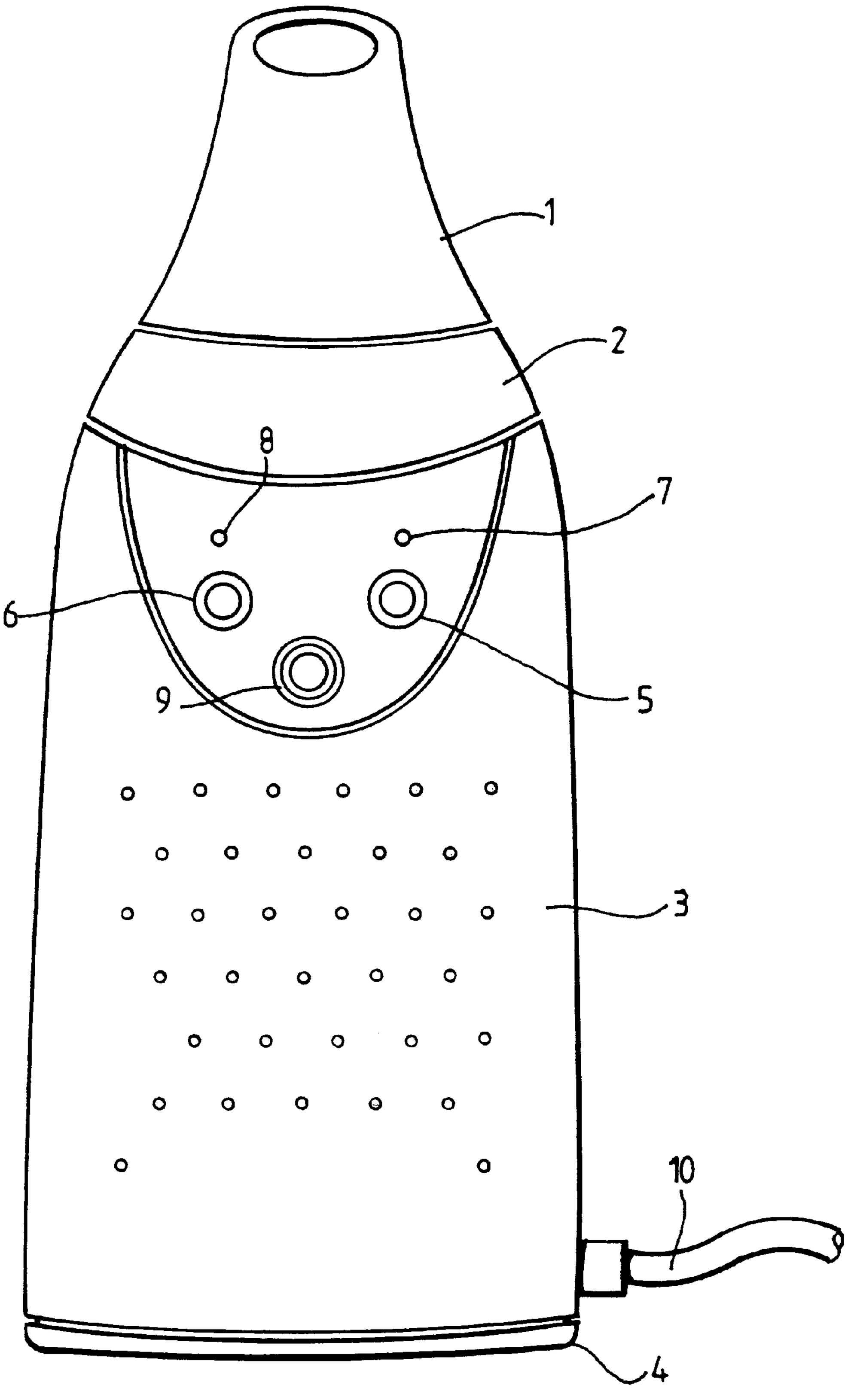
FIG. 1 shows a schematic view of a dispensing system according to the invention, complete with a nebulizer and mouthpiece fitted.

Referring to the figures, an embodiment of dispensing system according to the invention comprises a hand held dosimeter having a height of approximately 200 mm and a weight of approximately 200 g. The dosimeter has a mouthpiece (1) and a nebulizer (2) attached, and a body (3) which contains a control valve, electronic circuitry and a battery. These components can be accessed through base (4).

The dosimeter is connected to a compressed air source via tube (10). To operate the dosimeter, the patient removes mouthpiece (1), and pours a liquid form of the medication (which be a liquid or a powder in a fluidised form, or any other similar form) into the nebulizer (2). Then, the dosimeter is connected to the compressed air supply via tube (10). By means of a switch device to be described later, the presence of a positive pressure in the dosimeter activates the control circuitry in the dosimeter, and switches it on.

In this embodiment, although the nebulizer has only one well in which the medication sits, the dosimeter is nevertheless pre-programmed to deliver the correct dose of two different nominated drugs. The dosimeter could, however, be constructed and pre-programmed so as to deliver any desired number of nominated drugs. The drug which has been loaded into the nebulizer is selected using selector buttons (5) and (6). Once the drug type is selected, LED's (7) and (8) indicate the drug type selected by the patient. Button (9) is a re-set button, so that the user can correct any errors in selection.

The nebulizer used in the dispensing system according to the invention can be any suitable nebulizer design with a known calibration constant which is used to nebulize substances such as medicaments, which is suitably adapted to fit the dispensing system, and calibrated with the dosimeter. Suitable nebulizers include those which use a source of compressed air to nebulize the medicament, and are, for example, described in European Patent No. 672,266 (Medic-Aid Limited), the contents of which are incorporated by reference.

When the drug has been selected, the patient breaths in through mouthpiece (1). A pressure sensor (to be further described later) within body (3) detects a pressure drop within the mouthpiece (1) due to the patient's inhalation, and then delivers a pre-programme pulse of nebulized medicament into the first 50% of the inspiratory profile, until the dose regime programmed into the dispensing system has been delivered.

The dose is calculated from a known rate of output against time for the drug selected, and the sum of all the nebulizer pulses which the dosimeter has delivered. Further information on how the doses of drug may be derived and pre-programmed into the dosimeter may be obtained from GB 2,294,402 (Medic-Aid Limited et al), the contents of which are incorporated herein by reference. In this instance, clinical trials have been conducted to determine the dose of drug that must be delivered to achieve the correct therapeutic effect, and this dose has been programmed into the dosimeter for the two nominated drugs.

When the programmed dose has been delivered, the LED adjacent the button relating to the selected drug flashes rapidly and a buzzer sounds, indicating that the treatment is finished, and thereby ensuring that a precise dosage of drug is delivered to the patient on every occasion.

Figure 2:
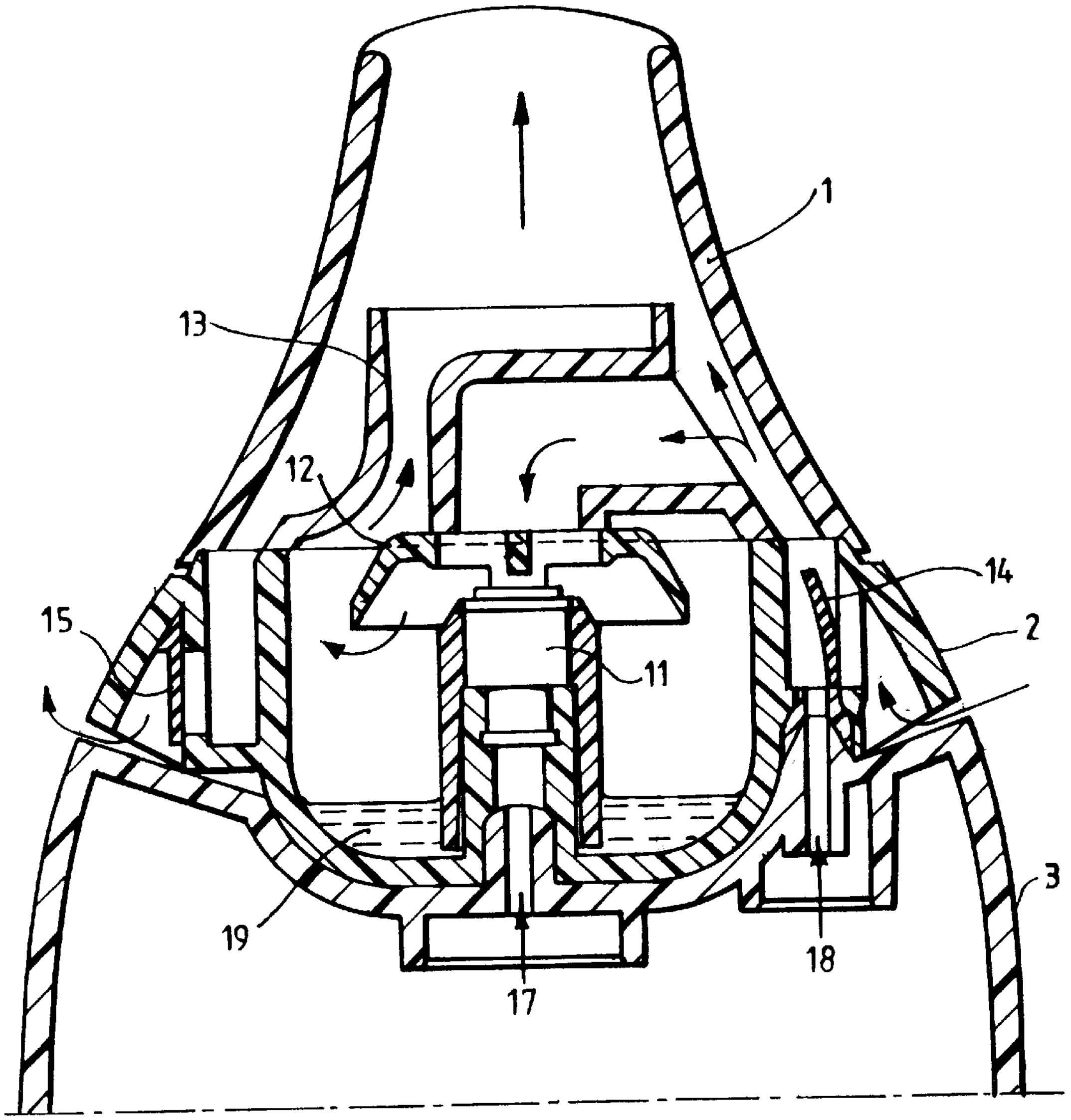
FIG. 2 shows a schematic cross-section view of the nebulizer/mouthpiece end of the dispensing system of FIG. 1.
Figure 3:
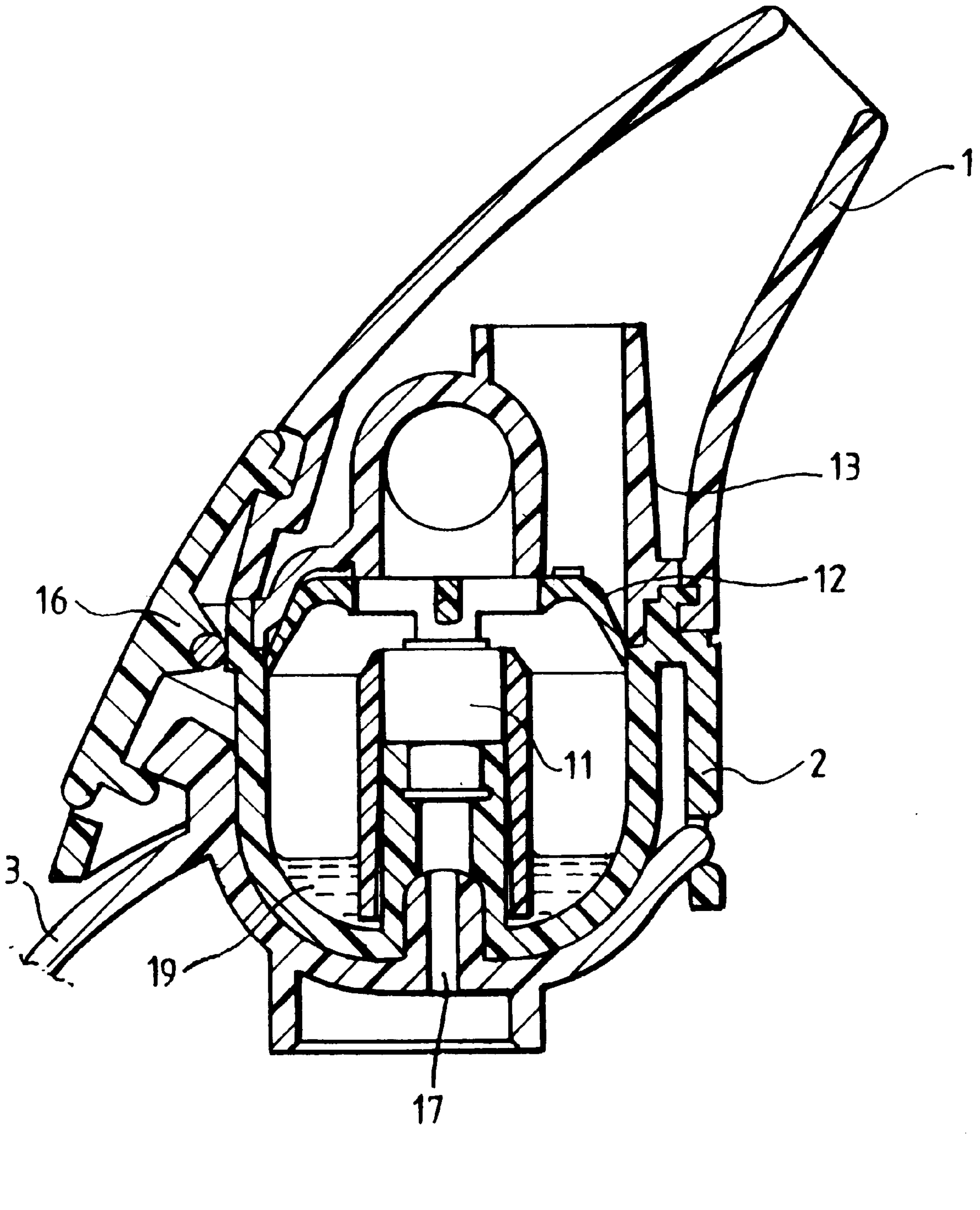
FIG. 3 shows a further schematic cross-section view of the nebulizer/mouthpiece end of the dispensing system of FIG. 1 from an orthogonal position to that shown in FIG. 2.

The nebulizer used in this embodiment is shown in more detail in FIGS. 2 and 3. Compressed air is supplied via port (17) to the nebulizer jet (11), and this works in conjunction with baffle (12) to aerosolize the liquid drug which has been placed in nebulizer bowl (19).

This nebulizer is venturi nebulizer which draws in air through the spout (13) into the centre of the baffle (12), and then up and out through the outlet of the spout (13) into the mouthpiece. As the nebulizer only generates aerosol during inspiration, the patients inhaled air is drawn through valve (14), and further through mouthpiece to the patient. A small proportion of this air is drawn down through the centre of the nebulizer to operate the venturi system. The flow through the nebulizer is completely independent of the patient's flow, and the nebulizer produces a constant rate of output. Valve (14) creates a pressure drop within the mouthpiece, and this is monitored through port (18). On exhalation valve (14) will close, and the patient will exhale through valve (15). Further information as the nebulizer on the nebulizer is contained in EP 627,266 (Medic-Aid Limited).

The complete assembly is held in place by catch (16). When the lower end of the catch is displaced the mouthpiece can be removed. The top end of the catch can then be tilted down to release the nebulizer bowl assembly from the main dosimeter case (3). This allows the whole nebulizer unit to be removed after the treatment has been completed, and cleaned completely separate from the main dosimeter case. This is further graphically illustrated in FIGS. 7 and 8.

Figure 4:
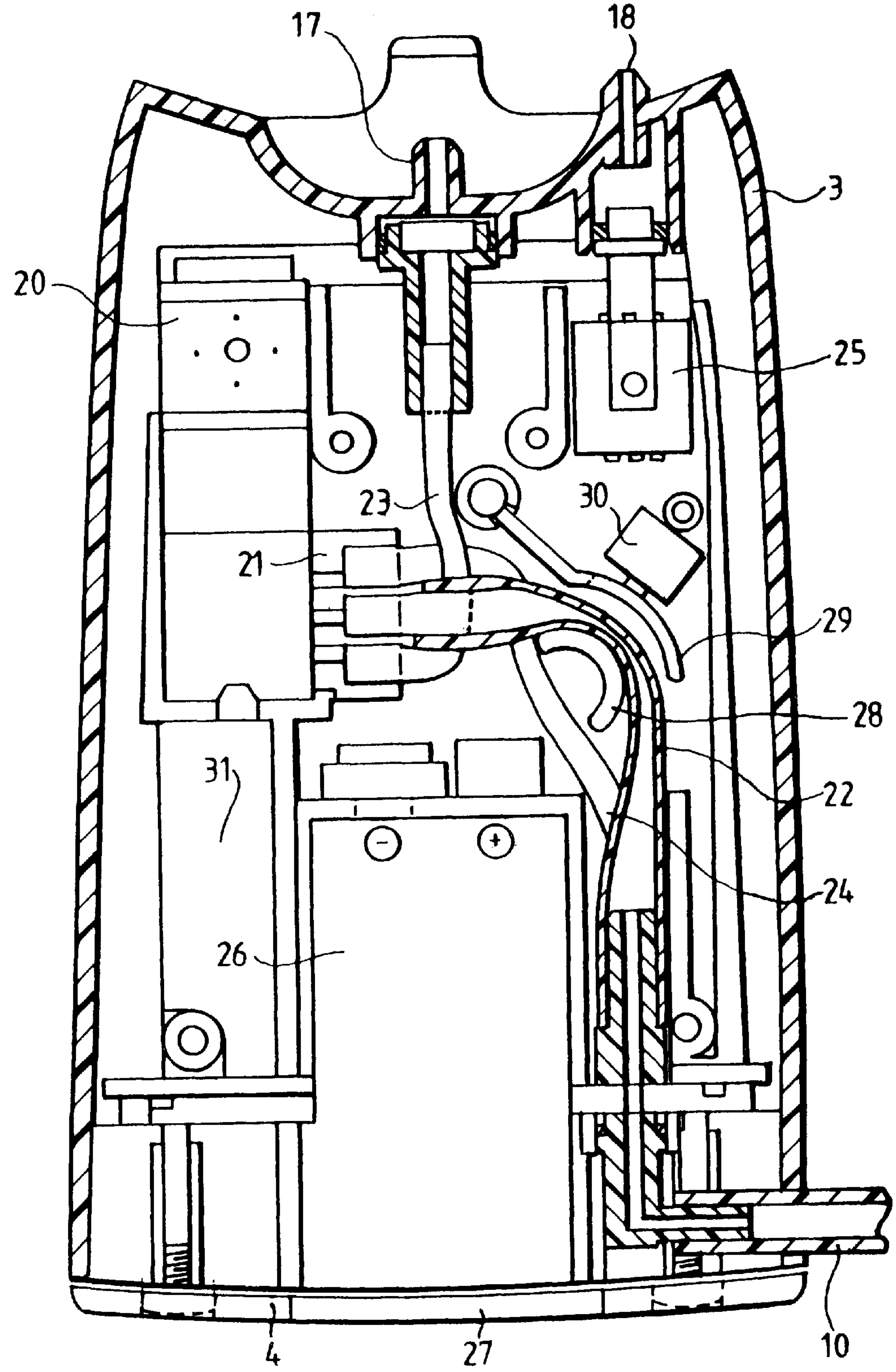
FIG. 4 shows a schematic cross-section view of the control system end of the dispensing system of FIG. 1.

FIG. 4 shows an internal section through the dosimeter, in particular showing the electronic configuration of the device. Air enters the dosimeter via tube (10) and through flexible tube (22) to the manifold (21) and onwards to valve (20). To determine whether there is pressure in the tube (22), it is configured around wall (28). When there is no pressure in the tube, the tube collapses. However, under pressure it expands, and moves lever (29) against switch (30), which switches the dosimeter on.

The dosimeter can be operated from various different compressed air sources; firstly it can use either a continuous air supply of approximately 6 litres per minute, generated from a conventional air compressor, or a compressed bottled gas supply such as is used in hospitals. With these compressed air sources, when the compressed air is not being supplied to the nebulizer via tube (23) and port (17), it must be vented externally through tube (24) out of the base of the dosimeter via an orifice which matches the size of the jet (11) diameter in the nebulizer. This maintains a constant pressure in the system irrespective of whether the valve is directing air to the nebulizer or the vent.

In an alternative and preferred embodiment, which can be used in conjunction with other forms of dosimeter, the dosimeter can be operated in conjunction with a low flow rate compressor system having a flow rate of 1–2 litres per minute, which has a fitted accumulator.

This compressor system generates a low flow of, for example, 1.5 litres per minute in the accumulator, and this allows the dosimeter to produce pulses of compressed air to the nebulizer with an equivalent flow rate of around 6 litres per minute, where the flow from the compressor is matched to the mean flow through the nebulizer (1.5 litres per minute). In this configuration tube (24) is sealed, and when the valve (20) is closed the pressure in the supply tube (10) is diverted into the compressor's accumulator. Port (18) connects the pressure sensor (25) to the mouthpiece. This is attached to the printed circuit board (31) which is powered by battery (26). When the electronic system detects the patient has inhaled, valve (20) diverts the pressure flow into tube (23) and out to a nebulizer via port (17). The battery is inserted into the dosimeter via door (27) into base (4).

Figure 5:
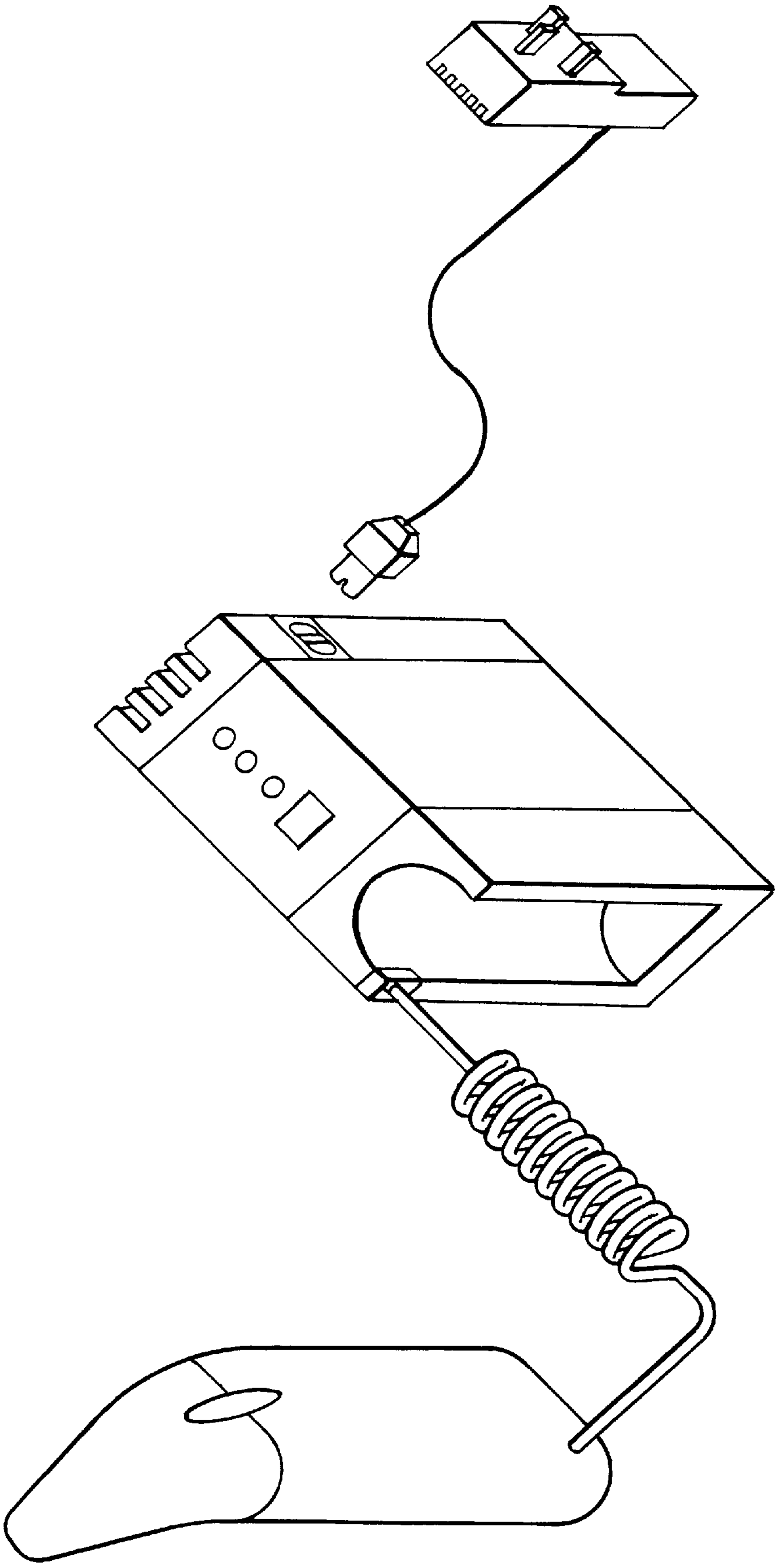
FIG. 5 shows a schematic view of the dispensing system of FIG. 1 attached to a low flow rate compressor.

An example of a suitable low flow rate compressor which can be used as described above is shown in FIGS. 5 and 6, and comprises a small air compressor with a flow of approximately 1.5 litres per minute, and an accumulator with a volume of about 0.2 litres, which may be formed, for example, in the tubing between the compressor and the dosimeter, or using a bellows and spring arrangement within the compressor casing. Below is described a rubber hemisphere accumulator which works particularly well. The compressor operates until the accumulator has reached its capacity, and then switches off. The dosimeter receives pulses of air from the accumulator until the accumulator has been emptied to a specified volume (0.1 litre). The compressor then cuts in and refills the accumulator. The compressor produces a mean output flow rate which is known to the dosimeter, and the dosimeter controls its supply of air so that it does not exceed the mean flow rate from the compressor, and any one pulse delivered by the dosimeter does not exceed accumulator capacity. This system therefore utilizes the compressor, which is approximately one-quarter of the size of a conventional compressor system, and one quarter of the energy requirement. Such a compressor is also cheaper to manufacture and provide.

Figure 9:
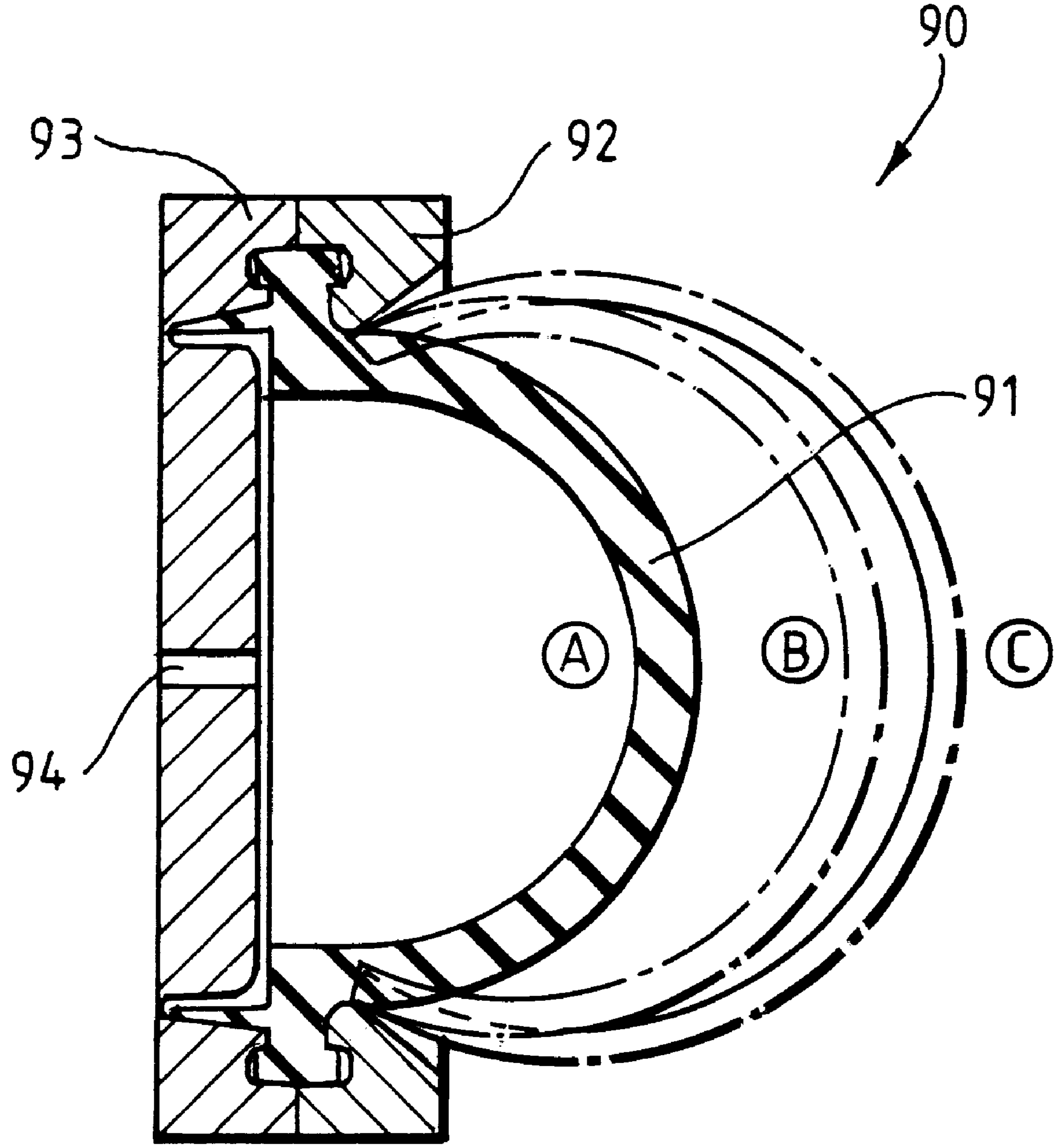
FIG. 9 shows an accumulator consisting of a generally hemispherical elastic diaphragm.

The accumulator in this embodiment should have a linear pressure to volume relationship over the period of a pulse delivery, which is typically 1.5 seconds long, with a nebulizer jet flow of 6 litres per minute, the accumulator should provide a volume flow of 150 millilitres at a constant pressure (1 bar+/−10%). It is difficult to obtain a steady linear pressure to volume relationship. FIG. 9 shows a natural rubber hemispherical accumulator. The rubber has a linear load to extension between an extension of 100% and 500%. A diaphragm 91 is a hemispherical component which is held trapped between two rings 92 and 93. In FIG. 9, the diaphragm is shown in three positions labelled A, B, C. Position A is the unloaded position from which the diaphragm starts and as compressed air is supplied via a port 94, the diaphragm expands to position C with a 200% extension. The compressed air supply is then stopped either by the actuation of a microswitch on the diaphragm surface (not shown) which stops the compressors, or by a pneumatic microswitch which then vents the compressor output. The diaphragm 91 then stays in this position until the valve sends a pulse of air to the nebulizer. When the diaphragm delivers air, the pressure drop during operation is less than 5%. The diaghragm can supply air at a stable pressure until it reaches position B which is a 120% extension. The microswitch would then restart the compressor, or the pneumatic microswitch would be closed. This hemisphere arrangement is relatively simple to manufacture, but has great advantages over other accumulator systems which might be used.

Figure 6:
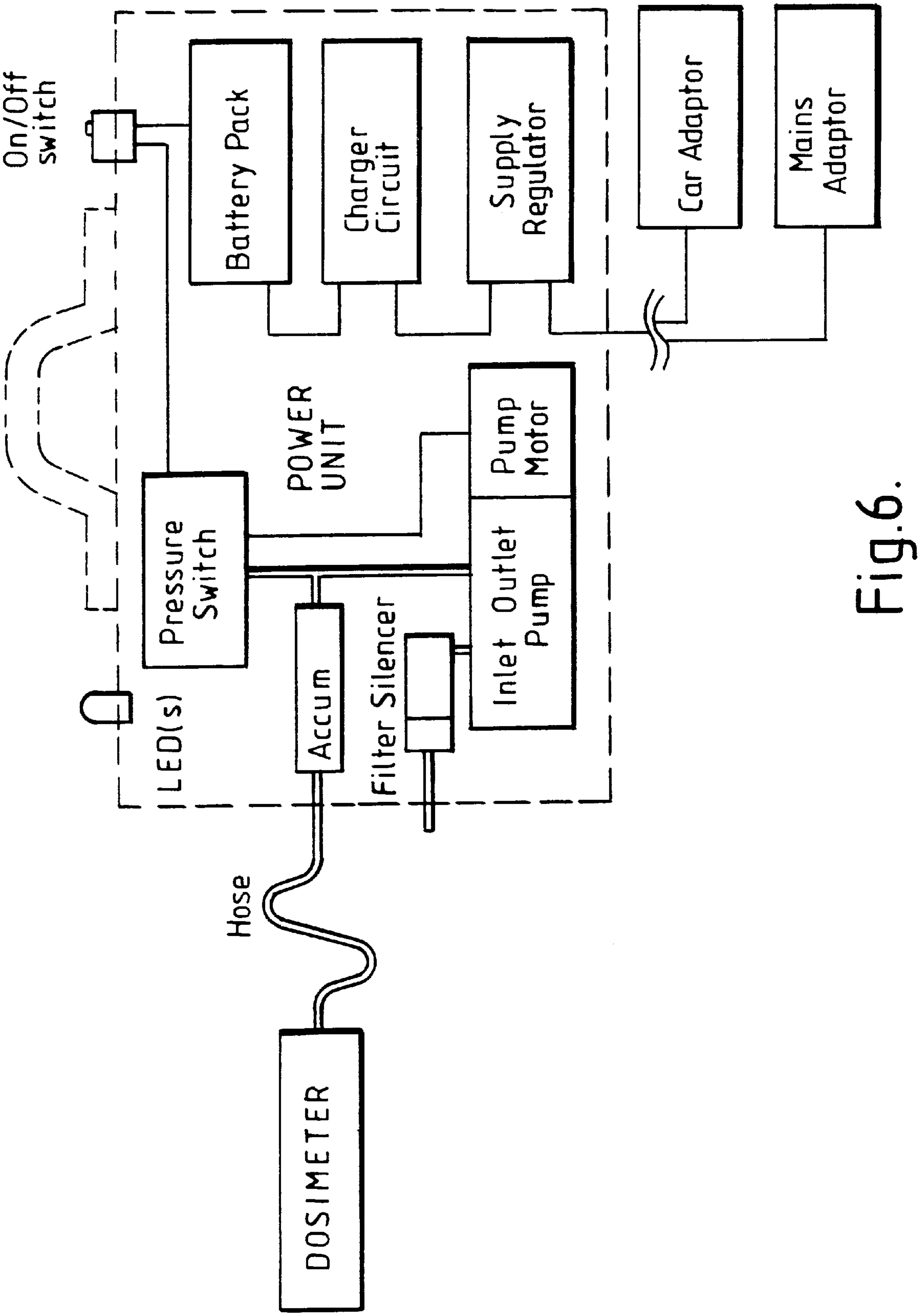
FIG. 6 shows a schematic representation of the combined dispensing system/compressor system of FIG. 5.
Figure 7A:
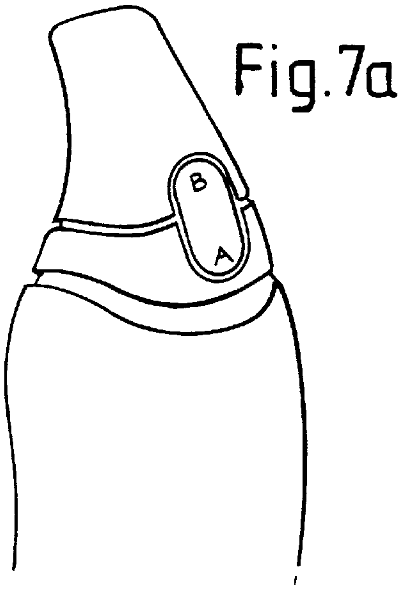
FIGS. 7*a*–7*d* shows a loading regime for loading an embodiment of dispensing system according to an aspect of the invention.
Figure 7B:
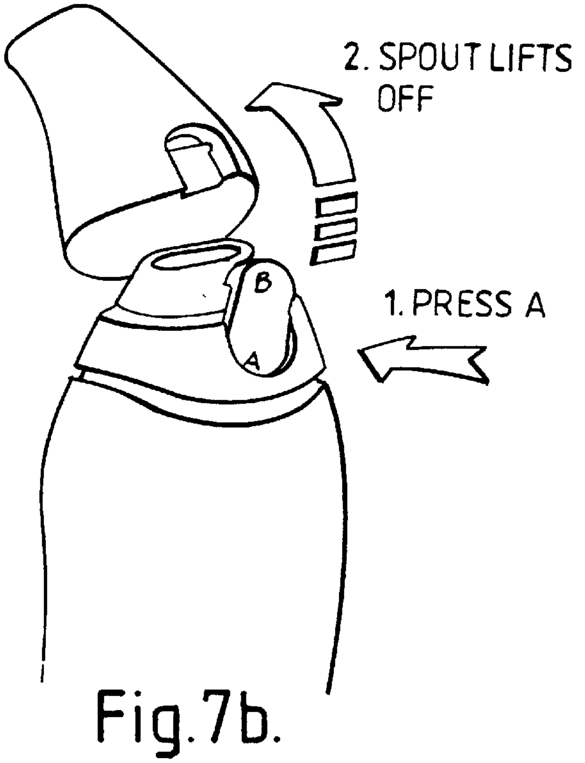
Figure 7C:
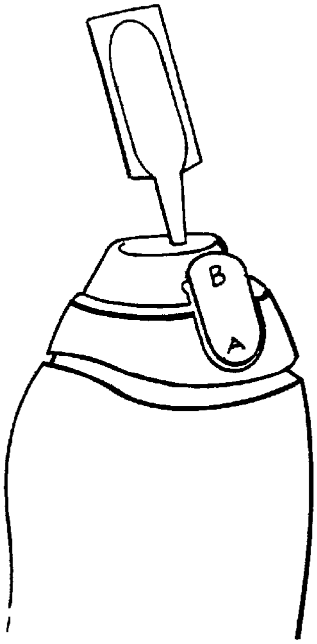
Figure 7D:
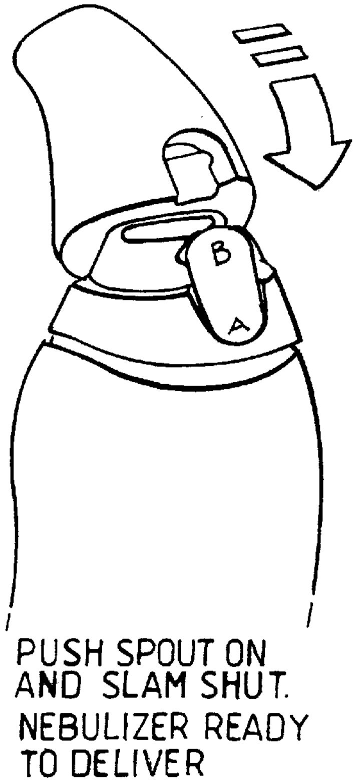
Figure 8A:
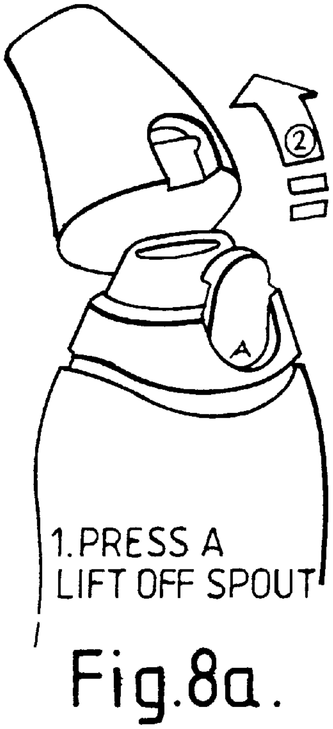
FIGS. 8*a*–8*d* shows cleaning regime for cleaning an embodiment of dispensing system according to an aspect of the invention.
Figure 8B:
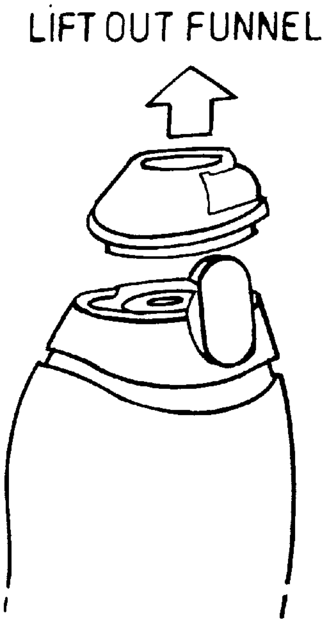
Figure 8C:
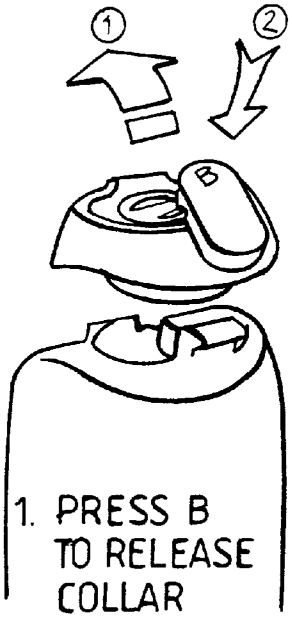
Figure 8D:
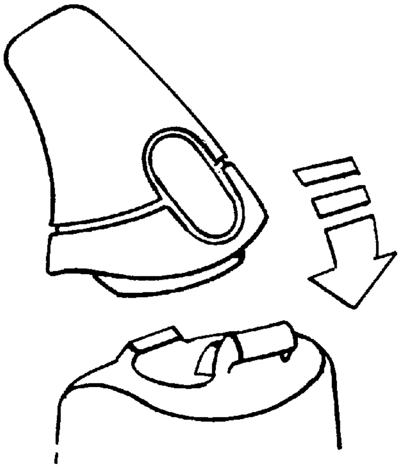

A suitable electrical configuration for such a compressor is shown in FIG. 6.

For the dispensing system according to the invention to work effectively, the dosimeter valve (20) should be in close proximity to the nebulizer, so that when the system detects the patient's inhalation, the nebulizer starts to work as quickly as possible, typically in less than 50 milliseconds. This means that the length of tube (23) between the manifold outlet and the nebulizer jet must be short, with an internal volume less than 0.7 ml, preferably less than 0.5 ml, which represents 5% of the shortest pulse the nebulizer delivers. If a long tube is used between the valve and the nebulizer, this tube has to be pressurized before the nebulizer starts to operate. This significantly affects the performance of the system, as to control the rate of output of the nebulizer it must be supplied with a "square wave" of air pressure, so that the output is constant over time, and is delivered at the start of inhalation. The nebulizer delivers pulses to inspiratory patterns between 0.1 and 1.5 seconds' duration.

One of the simplest ways of determining the dose of medicament which is received by the patient is, as described as above, to multiply the nebulizer output rate by the duration of each pulse. The doses then ascertained by summing the amount of medicament which is received during each pulse. This calculation relies on the fact that the output rate of a nebulizer should be constant regardless of the rate of inhalation of the patient. Therefore, provided that the nebulizer output rate is the same for a person who inhales slowly as for a patient who inhales quickly, the calculation will be accurate. If the nebulizer output rate varies with the speed of inhalation, the precision of the dosimeter will vary.

Figure 10:
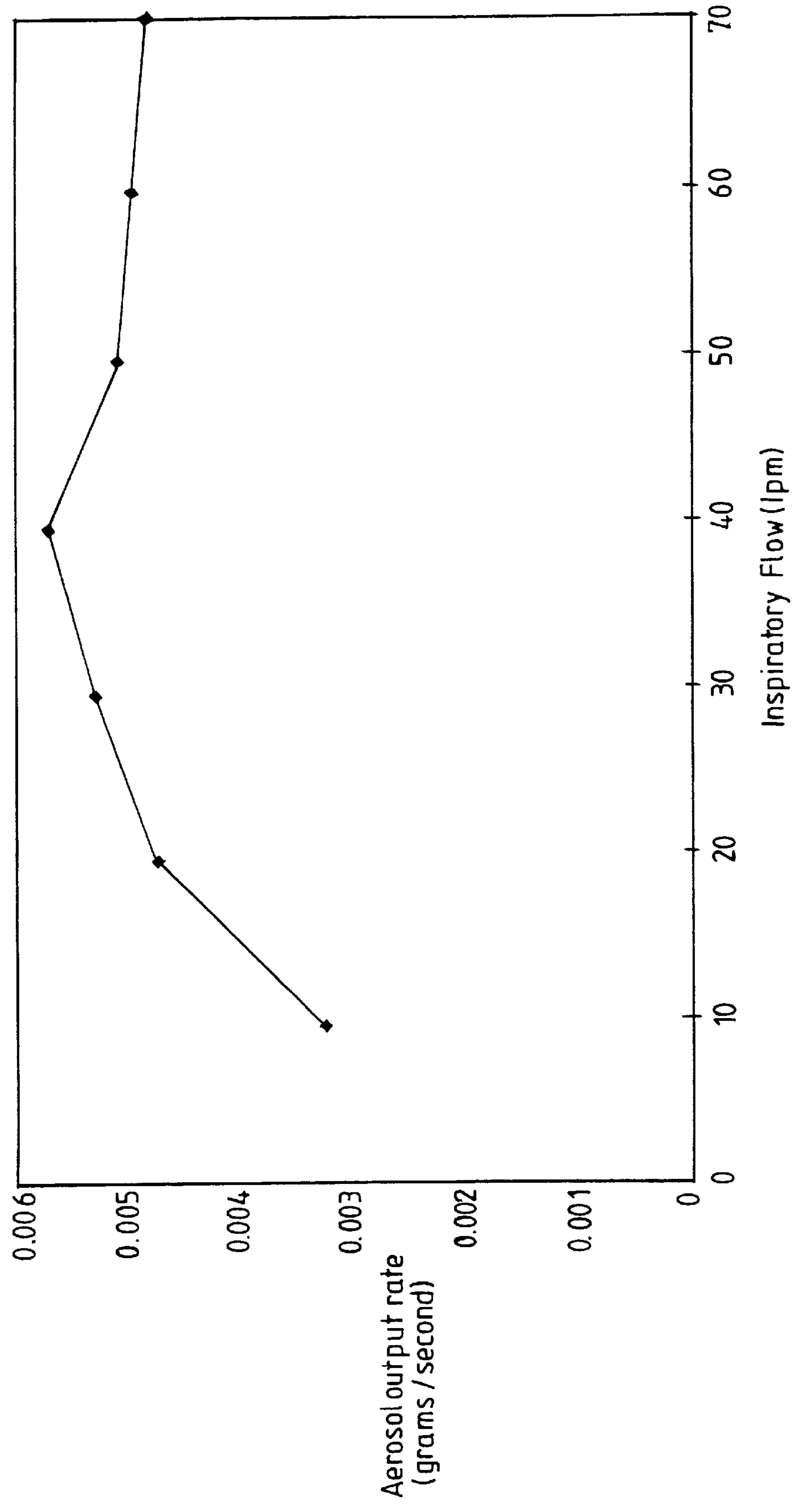
FIG. 10 is a graph showing the nebulizer output rate of a typical nebulizer against the inspiratory flow of a patient.

FIG. 10 is a graph showing the variation of aerosol output rate with the speed of inspiratory flow for a typical nebulizer. As will be seen, the output is not constant.

It is therefore proposed to use the pressure sensor to provide information on the patient flow rate so that the correct nebulizer calibration rate is determined during patient inhalation. This may be done in the from of a look-up table which is quite effective, and the look-up table can have two or more calibration points as required to provide the necessary accuracy. A satisfactory look-up table can be achieved by using an approximation of the look-up table which, in the case of the graph shown in FIG. 10 can be made up of two straight lines, one line generally following the curve to the 30 lpm point and a second line which generally follows the curve above that. Such an approximation works well because, in reality, the breathing pattern of a patient is not at a fixed level, but is continually changing.

Another way of using the correct calibration value is to use the computer which takes the inspiratory flow rate into account. One calibration value can be used above the 30 litres per minute level, and when the flow is below about 15 litres per minute, then the calibration constant is reduced to 60% of that value. Thus, the calibration may be achieved in a number of different ways not just a multi-point look-up table.

While the invention has been described above with reference to specific embodiments thereof, it is apparent that many changes, modifications and variations can be made herein. Accordingly, it is intended to embrace all such changes, modifications and variations that fall within the spirit and broad scope of the appended claims. All of the above-noted patents, patent applications and publications referred to in this application are incorporated herein by reference in their entireties.

What is claimed is:

1. A product dispensing system comprising:

a calibrated nebulizer having a nebulizer jet;

a mouthpiece;

means for sourcing compressed air;

a manifold for distributing the compressed air in at least one direction;

a port;

a nebulizer accommodation means which is accessed by the port;

a valve means for controlling the manifold and thereby the flow of compressed air to the port; and a length of tube linking the manifold and the port, the internal volume of which, from the manifold outlet to the nebulizer jet, is less than 0.7 ml.

2. A dispensing system as claimed in claim 1, wherein the manifold is integral with the valve means.

3. A dispensing system as claimed in claim 1, additionally comprising a compressor having a flow rate of 1–2 liters per minute and an accumulator.

4. A dispensing system as claimed in claim 1, additionally comprising a switch means which is responsive as to whether compressed air is flowing in the system.

5. A dispensing system as claimed in claim 1, further comprising a dosimeter which has been pre-programmed to dose one or more medicaments according to predetermined dosage profiles.

6. A dispensing system according to claim 1, further comprising a pressure sensor which is capable, in use, of detecting a pressure drop in the apparatus in response to the patient's breathing, whereby a pulse of nebulized medicament may be delivered into the mouthpiece.

7. A dispensing system according to claim 6 further comprising means for calculating the dosage of medicament on the basis of the known rate of medicament output against time for the selected drug.

8. A dispensing system according to claim 1, wherein the manifold is an integral part of the valve means.

9. A dispensing system according to claim 1, where the manifold is a shaped block with integral galleys the presence of which allows the tubes to be connected to the ports on the valve.

10. A dispensing system according to claim 1, further comprising a lightweight compressor system and an accumulator.

11. A dispensing system according to claim 10, wherein the lightweight compressor generates a low flow rate of the order of 1 to 2 liters per minute.

12. A dispensing system according to claim 10 wherein the combination of the low flow rate compressor and the accumulator allows the dispensing system to produce pulses of compressed air to the nebulizer with a flow of around of 6 litres per minute.

13. A dispensing system according to claim 12 wherein the combination of the low flow rate compressor and the accumulator allows the dispensing system to produce pulses of compressed air to the nebulizer with a flow of around of 6 litres per minute.

14. A dispensing system according to claim 11, wherein the valve means serves to switch the compressed air on and off.

15. A dispensing system according to claim 1, wherein the manifold together with the valve means serve to direct the flow of compressed air either to the nebulizer or to an outlet orifice.

16. A dispensing system according to claim 1, wherein the volume of the tube linking the manifold outlet to the nebulizer jet is less than 0.5 ml.

17. A dispensing system according to claim 1, wherein the nebulizer serves to deliver inspiratory pulses between 0.1 and 1.5 second in duration.

18. A dispensing system according to claim 10, wherein the accumulator includes an resilient elastic body having a generally linear pressure to volume relationship.

19. A dispensing system according to claim 18, wherein the resilient body is a generally hemispherical resilient element.

20. A dispensing system according to claim 19 wherein the hemispherical element is a diaphragm extendable to 500% of its unloaded volume.

21. A product dispensing system comprising:

a calibrated nebulizer having a nebulizer jet;

a mouthpiece;

means for sourcing compressed air;

a manifold for distributing the compressed air in at least one direction;

a port;

a nebulizer accommodation means which is accessed by the port;

a valve means for controlling the manifold and thereby the flow of compressed air to the port;

a length of tube linking the manifold and the port;

a compressor; and an accumulator;

wherein the accumulator includes a resilient elastic body having a generally linear pressure to volume relationship.

22. A product dispensing system according to claim 21 wherein the internal volume of the tube from the manifold outlet to the nebulizer jet is less than 0.7 ml.

23. A product dispensing system comprising:

a calibrated nebulizer having a nebulizer jet;

a mouthpiece;

means for sourcing compressed air;

a manifold of distributing the compressed air in at least one direction;

a port;

a nebulizer accommodation means which is accessed by the port;

a valve means for controlling the manifold and thereby the flow of compressed air to the port;

a length of tube linking the manifold and the port;

a pressure sensor for detecting a drop in pressure in the apparatus in response to a patient's breathing to indicate the rate of inhalation of the patient; and means for determining the dose dispensed, the dose being determined on the basis of the output rate of the medicament of the nebulizer, and the duration of the delivery of the medicament, the dose determining means serving to adjust the value of the output rate on the basis of the rate of inhalation of the patient detected by the pressure sensor.

24. A system according to claim 23, wherein the internal volume of the tube from the manifold outlet to the nebulizer jet is less than 0.7 ml.

* * * * *